United States Patent
Shah et al.

[19]

[11] Patent Number: 5,941,850
[45] Date of Patent: Aug. 24, 1999

[54] SAFETY CANNULA

[76] Inventors: Binod Shah, 269-10 Grand Center Pkwy., Mail #CE, Floral Park, N.Y. 11005; Sujata Shah; Bilkram P. Shah, both of 11/234, Janakpurdham, Nepal

[21] Appl. No.: 09/107,569

[22] Filed: Jun. 29, 1998

[51] Int. Cl.$^6$ .................................................. A61M 5/00
[52] U.S. Cl. .......................... 604/110; 604/272; 604/164
[58] Field of Search .................................. 604/272, 187, 604/158, 162, 164, 198, 110

[56] References Cited

U.S. PATENT DOCUMENTS

| | | | |
|---|---|---|---|
| 4,154,242 | 5/1979 | Termanini | 128/349 |
| 4,828,548 | 5/1989 | Walter | 604/164 |
| 5,024,665 | 6/1991 | Kaufman | 604/179 |
| 5,207,647 | 5/1993 | Phelps | 604/158 |
| 5,407,431 | 4/1995 | Botich et al. | 604/110 |

*Primary Examiner*—Wynn Wood Coggins
*Assistant Examiner*—N. Kent Gring

[57] ABSTRACT

The present invention is anti prick needle which is extendable and retractable only under positive user control. The present invention has an auto stopper that prevents inadvertent extension of the needle to an operable position without user invention. In operation the present invention is fitted to the end of a syringe. The user pushes down on an extending device which releases a latching device permitting the needle to slide forward to an operable position against a spring bias. The needle remains extended as long as the user continues to push on the extending device. When the user has completed an injection and releases the extending device the needle is automatically retracted by the spring bias. Further, once the needle is retracted into the needle holder an auto stopper latching device is activated which closes the opening preventing the needle from being extended with the extending device or other means.

9 Claims, 5 Drawing Sheets

SAFETY CANNULA

BACKGROUND OF THE INVENTION

1. Field of the Invention

The present invention relates to medical devices. More particularly, the present invention relates to safety needles.

2. Description of the Prior Art

A major concern in the medical community is an inadvertent needle prick. There are numerous cases of health care workers becoming infected with deadly diseases after pricking with a used needle. While great care is used to account for all needles because of the vast number used each day a small percentage will be missplaced. Further, the use of needles with patients in agony or volent increases the risk of a prick. What is needed is a simple device which is inexpensively manufacturable that protects the health care worker from inadvertent needle pricks.

Numerous innovations for safety cannula have been provided in the prior art that are described as follows. Even though these innovations may be suitable for the specific individual purposes to which they address, they differ from the present invention as hereinafter contrasted.

In U.S. Pat. No. 5,407,431, titled Intravenous Catheter Insertion Device, invented by Michael J. Botich and Thor Halseth, a hypodermic injection system is described having with a retractable needle wherein the needle retracts within an interior cavity of a syringe plunger, such that the needle is confinedly held within the plunger. A cylindrical spring housing assembly has resilient fingers which captures a spring biasly holding a needle holder against the retaining force of resilient fingers. The plunger has a frangible end, which dissociates when the outwardly tapered shoulders spread the resilient fingers, allowing the coiled spring to eject the needle and its holder into the interior cavity of the plunger. A body fluid sampling embodiment employs the same functional elements except the plunger is shorter and contains a linking that communicates with a vacuum container. The container allows fluid sampling and provides the structure to release the spring retracting the needle. The retractable needle embodiment is also employed with an insertion needle that guides a catheter tube below the skin of a patient and into the vein, and allows retraction of the insertion needle thereby avoiding accidental pricking of the health care worker by the insertion needle.

The patented invention differs from the present invention because the patented invention is a retractable needle that retracts within an interior cavity of a syringe plunger. A cylindrical spring housing assembly has resilient fingers which captures the needle preventing extension. When the plunger is pushed, the needle is extended against a spring bias. Withdrawing the plunger allows fluid sampling and provides the structure to release the spring retracting the needle. When the plunger is withdrawn beyond a preselected limit, the needle is released and automatically withdrawn into the housing. The patented invention functions with a plunger and needle which cooperate together. The present invention functions with any device to which a needle is adapted. The present invention has an auto stopper that prevents inadvertent extension of the needle to an operable position without user intervention. In operation the present invention is fitted to the end of a syringe. The user pushes down on an extending device which releases a latching device permitting the needle to slide forward to an operable position against a spring bias. The needle remains extended as long as the user continues to push on the extending device. When the user has completed an injection, and releases the extending device the needle is automatically retracted by the spring bias. Further, once the needle is retracted into the needle holder an auto stopper latching device is activated which closes the opening preventing the needle from being extended with the extending device or other means.

In U.S. Pat. No. 5,207,647, titled Needle Device, invented by David Y. Phelps, a needle device for delivering medicaments to the body of a patient, the device including an elongated housing having a catheter on one end, with a trocar arranged through the end of the housing and the catheter. The trocar is reciprocably advancable and retractable with respect to the catheter. A spring biased carriage in the housing controls the movement of the trocar and causes it to retract from the distal end of the catheter after the catheter and trocar have been advanced into a body and the trocar no longer encounters resistance to forward or distally directed advance of the device.

The patented invention differs from the present invention because the patented invention is a needle device that includes an elongated housing having a catheter on one end, with a trocar arranged through the end of the housing and the catheter. The trocar is advancable and retractable with respect to the catheter. A spring biased carriage in the housing controls the movement of the trocar and causes it to retract from the distal end of the catheter after the catheter and trocar have been advanced into a body and the trocar no longer encounters resistance to forward or distally directed advance of the device. The present invention has an auto stopper that prevents inadvertent extension of the needle to an operable position without user intervention In operation the present invention is fitted to the end of a syringe. The user pushes down on an extending device which releases a latching device permitting the needle to slide forward to an operable position against a spring bias. The needle remains extended as long as the user continues to push on the extending device. When the user has completed an injection and releases the extending device the needle is automatically retracted by the spring bias. Further, once the needle is retracted into the needle holder an auto stopper latching device is activated which closes the opening preventing the needle from being extended with the extending device or other means.

In U.S. Pat. No. 5,024,665, titled Composite Catheter Assembly, invented by Jerry M. Kaufman, a composite catheter assembly for fixing, locating, inserting and accurately securing intravenous catheters having a needle thereon within body fluid conduits has an attachment plate with an elongated opening therein, a barrel having a bore extending inwardly from one open end of the barrel to define a transverse shoulder so that a passage or sized opening can be provided between the bore and the exterior of the barrel at the transverse shoulder end of the bore, a catheter assembly including, a carrier is slidably mounted in the bore of the barrel for movement of the needle on the catheter assembly from a retracted position in the barrel to an extended position into the body fluid conduit. A retracting assembly is provided which includes, a spring that is compressed when the catheter assembly is moved from the retracted position to the extended position, and an operatively associated locking and latching assembly to hold and releasably lock the catheter assembly in the extended position and when actuated to permit the compressed spring to retract the catheter assembly and withdraw the needle until it is returned to the retracted position in the barrel.

The patented invention differs from the present invention because the patented invention is a composite catheter which includes, a spring that is compressed when the catheter assembly is moved from the retracted position to the extended position, and an operatively associated locking and latching assembly to hold and releasably lock the catheter assembly in the extended position and when actuated to permit the compressed spring to retract the catheter assembly and withdraw the needle until it is returned to the retracted position in the barrel. The present invention has an auto stopper that prevents inadvertent extension of the needle to an operable position without user intervention. In operation the present invention is fitted to the end of a syringe. The user pushes down on an extending device which releases a latching device permitting the needle to slide forward to an operable position against a spring bias. The needle remains extended as long as the user continues to push on the extending device. When the user has completed an injection and releases the extending device the needle is automatically retracted by the spring bias. Further, once the needle is retracted into the needle holder an auto stopper latching device is activated which closes the opening preventing the needle from being extended with the extending device or other means.

In U.S. Pat. No. 4,828,548, titled Safety Catheter, invented by Gregory W. Walter, a disposal apparatus is described for the safe disposal of a medicinal needle after use utilizing a container with a vacuum therein and a piston attached to one side of the needle which protrudes ready for use. After use of the needle, one side of the piston is exposed to ambient pressure and the needle is retracted into the container for safe disposal. A sight chamber attached to said piston within said container and communicating with said needle indicates when said needle has pierced a blood vessel. In another embodiment, a spring is employed to retract the needle.

The patented invention differs from the present invention because the patented invention is a disposal apparatus is described for the safe disposal of a medicinal needle. The patented invention lacks features similar to the present invention.

In U.S. Pat. No. 4,154,242, titled Bladder Catheter, invented by Zafer A. Termanini, an improved bladder catheter for insertion in a body cavity comprises a tubular member having a distal end and a proximal end, a longitudinally extending lumen open for drainage at the proximal end, and a plurality of circumferentially spaced longitudinally extending slits adjacent the distal end. At least the portion of the tubular member intermediate the extremities of the slits is flexible and at least one longitudinally extending spring element is disposed in each of the intermediate portions, the spring elements being unstressed when the intermediate portions are flush with the adjacent unslitted portions of the tubular member for biasing the intermediate portions to the flush position. The improved catheter also includes means within the tubular member for releasably retracting the distal end relative to the proximal end to flex the intermediate portions outwardly from the adjacent portions for retaining the catheter in the bladder. Upon release of the retracting means, the spring elements return to their unstressed state thereby returning the intermediate portions to the flush position to permit catheter withdrawal.

The patented invention differs from the present invention because the patented invention is a bladder catheter having a spring element which is unstressed prior to insertion into a body. When the bladder catheter is inserted into a body, a spring is biased to hold the catheter in position. Upon release of the bladder catheter, the spring elements return to their unstressed state to permit catheter withdrawal. The present invention has an auto stopper that prevents inadvertent extension of the needle to an operable position without user intervention. In operation the present invention is fitted to the end of a syringe. The user pushes down on an extending device which releases a latching device permitting the needle to slide forward to an operable position against a spring bias. The needle remains extended as long as the user continues to push on the extending device. When the user has completed an injection and releases the extending device the needle is automatically retracted by the spring bias. Further, once the needle is retracted into the needle holder an auto stopper latching device is activated which closes the opening preventing the needle from being extended with the extending device or other means.

Numerous innovations for safety cannula have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is anti prick needle which is extendable and retractable only under positive user control. The present invention has an auto stopper that prevents inadvertent extension of the needle to an operable position without user intervention. In operation the present invention is fitted to the end of a catheter. The user pushes down on an extending device which releases a latching device permitting the needle to slide forward to an operable position against a spring bias. The present invention is manufactured attached to a catheter with a needle in an operable position. In use, the user removes a catheter cover and inserts the catheter into a patient. The needle remains extended as long as the user continues to push on the extending device. A cap may be removed by the user to test the connection to the blood stream. When the user has completed an insertion and releases the extending device the needle is automatically retracted by the spring bias. Once the needle is retracted into the needle holder and removed from the catheter, an auto stopper latching device is activated which closes the opening preventing the needle from being extended without being inserted into the catheter. A second latching device prevents the extending device from redeploying the needle with out both releasing the extending device and the second latching device.

The types of problems encountered in the prior art are injury and infection to health care workers due to inadvertant needle pricks.

In the prior art, unsucessful attempts to solve this problem were attempted namely: complex, expensive and ineffective devices or procedures. However, the problem was solved by the present invention because the needle tip is autmatically retrated into a protected area.

Innovations within the prior art are rapidly being exploited as numerous devices are developed to protect heath care workers from needle pricks.

The present invention went contrary to the teaching of the art because the present invention double interlocks when the needle retracts.

The present invention solved a long felt need for a needle that is inexpensive to manufacturer and prevents inadvertant pricks of health care workers.

Accordingly, it is an object of the present invention to provide a needle which is automatically withdrawn into a housing after use.

More particularly, it is an object of the present invention to provide a needle biased to retract and a interlock which prevents reextension of the needle after use.

In keeping with these objects, and with others which will become apparent hereinafter, one feature of the present invention resides, briefly stated, in a housing which contains a needle, needle retraction means and an interlock device.

In accordance with another feature of the present invention, a lock has a lock button which is attached to a lock pin which is biased to an ititial position by a lock spring.

Another feature of the present invention is that a stopper, positioned in a housing front, pivoitally rotates around a stopper pin functioning to prevent reextension of a needle after retraction.

Yet another feature of the present invention is that a retainer is biased by a spring.

Still another feature of the present invention is that a lock in a first position engages and prevents the retainer from moving. The lock in a second position releases the retainer.

Still yet another feature of the present invention is that a connector, attached to the rear of the safety cannula is removably attached to the cap.

Another feature of the present invention is that the needle is slidably attached to the interior of the housing.

Yet another feature of the present invention is that a cover protects the end of the safety cannula.

Another feature of the present invention is that a lock button, when depressed, has a pair of slots which engage the housing middle slot permitting the lock button to slide between a housing rear opening and a housing front opening.

The novel features which are considered characteristic for the invention are set forth in the appended claims. The invention itself, however, both as to its construction and its method of operation, together with additional objects and advantages thereof will be best understood from the following description of the specific embodiments when read and understood in connection with the accompanying drawings.

LIST OF REFERENCE NUMERALS UTILIZED IN THE DRAWINGS
COMMON COMPONENTS
14—needle (14)
14F—needle front (14F)
14R—needle rear (14R)
16—retainer (16)
16F—retainer front (16F)
16R—retainer rear (16R)
18—first spring (18)
20—cap (20)
20F—cap front (20F)
20R—cap rear (20R)
22—connector (22)
22F—connector front (22F)
22R—connector rear (22R)
24—lock (24)
24A—lock button (24A)
24B—lock pin (24B)
24C—lock spring (24C)
26—stopper (26)
26A—stopper pin (26A)
28—catheter (28)
30—latch (30)
FIRST EMBODIMENT
110—first safety cannula (110)
112—first housing (112)
112F—first housing front (112F)
112FA—first housing front opening (112FA)
112R—first housing rear (112R)
112RA—first housing rear opening (112RA)
112M—first housing middle (112M)
112MA—first housing middle divider (112MA)
112MB—first housing middle indent (112MB)
112AR—first housing slot rear opening (112AR)
112AM—first housing slot middle opening (112AM)
112AF—first housing slot front opening (112AF)
SECOND EMBODIMENT
210—safety cannula (210)
212—housing (212)
212F—housing front (212F)
212FA—housing front opening (212FA)
212R—housing rear (212R)
212RA—housing rear opening (212RA)
212M—housing middle (212M)
212MA—housing middle divider (212MA)
212MB—housing middle indent (212MB)
212AR—housing slot rear opening (212AR)
212AM—housing middle slot (212AM)
212AF—housing slot ront opening (212AF)
232—second cap (232)

DESCRIPTION OF THE PREFERRED EMBODIMENT

Figure 1:
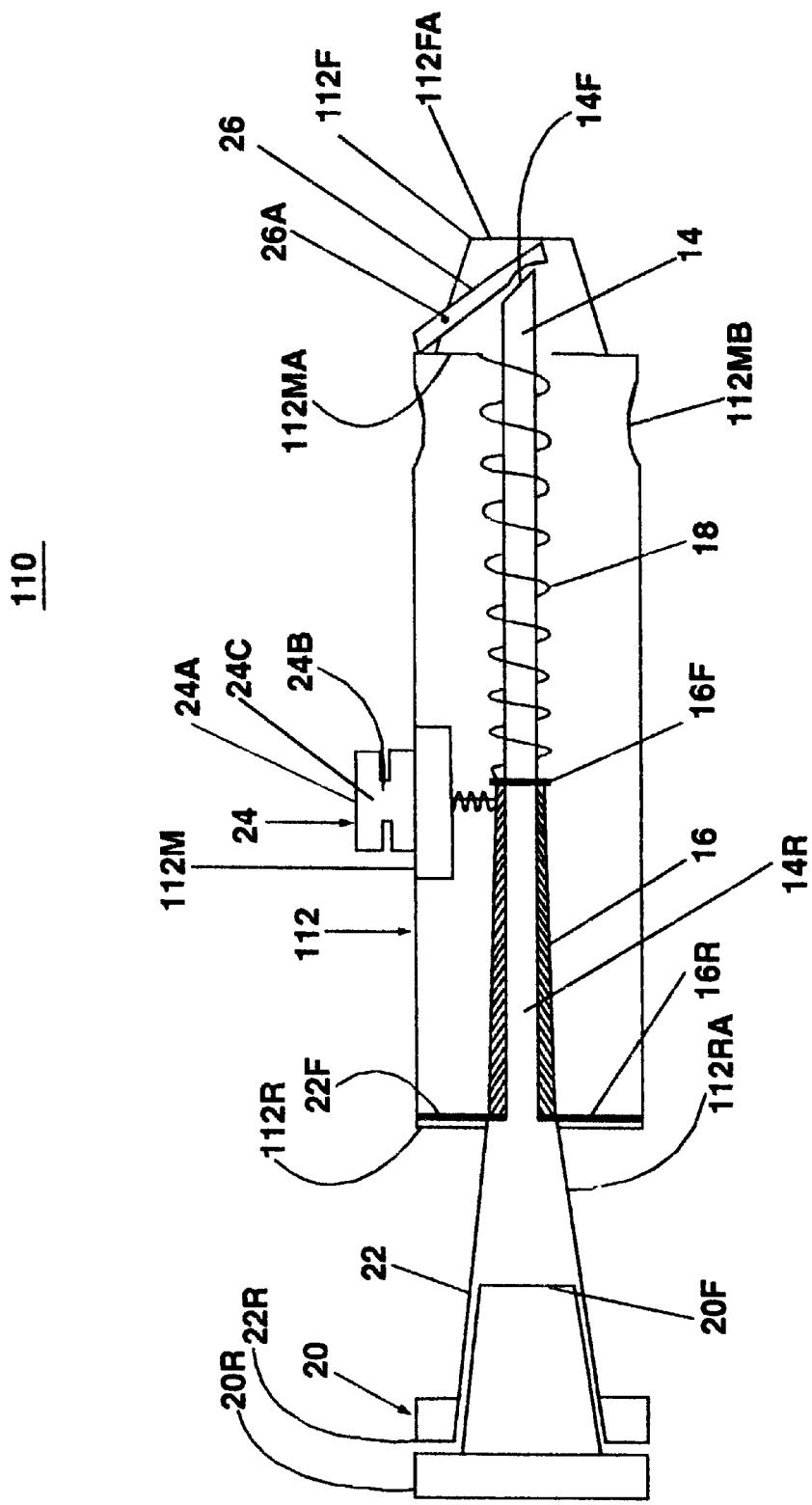
FIG. 1 is a cross-sectional view of a safety cannula with a needle in a operable position.

Firstly, referring to FIG. 1 which is a cross-sectional view of a first safety cannula (110) with a needle (14) in a safe position. The first safety cannula (110) comprises a first housing (112) which comprises a first housing front (112F). The first housing front (112F) comprises a first housing front opening (112FA) centrally positioned therein. The first housing front (112F) further comprises a first housing rear (112R) having a first housing rear opening (112RA). The first housing front (112F) filter comprises a first housing middle (112M) with a first housing middle divider (112MA) having an opening centrally positioned therein. The first housing middle (112M) further comprises a first housing middle indent (112MB) which functions as a gripping means.

The first housing middle (112M) further comprises a first housing rear opening (112AR) on an upper side which is connected to a first housing middle slot (112AM). The first housing middle slot (112AM) is connected to a first housing front opening (112AF).

The first housing front (112F) further comprises a stopper (26) which is pivotally positioned on a stopper pin (26A). The first housing front (112F) further comprises a complimentary shaped removable catheter (28).

The first safety cannula (110) further comprises a needle (14) which is slidably positioned within the first housing (112). The needle (14) comprises a needle front (14F) and a needle rear (14R). The first safety cannula (110) further comprises a retainer (16) which is securely connected to the needle rear (14R). The retainer (16) comprises a retainer front (16F) and a retainer rear (16R). The first safety cannula (110) further comprises a first spring (18) which is positioned around the needle (14) between the retainer front (16F) and the first housing middle opening divider (112MA). The first safety cannula (110) further comprises a connector (22). The connector (22) comprises a connector rear (22R) and a connector front (22F) which are removably and securely positioned in the first housing rear opening (112RA). The connector rear (22R) and a connector front (22F) are sealably attached to the retainer rear (16R). The first safety cannula (110) further comprises a cap (20). The cap (20) comprises a cap front (20F) which is removably and securely positioned in the connector rear (22R). The cap (20) comprises cap rear (20R) which is connected to an IV tube.

The first safety cannula (110) further comprises a lock (24) which is movably positioned in the first housing middle (112M). The lock (24) comprises a lock button (24A) having a middle pair of middle grooves and having a lock pin (24B) securely attached thereto and extending therefrom. The lock (24) further comprises a lock spring (24C) which is positioned around the lock pin (24B) on an inside of the first housing middle (112M). The lock button (24A) is slidable attached to the first housing slot rear opening (112AR) which is connected to a first housing middle slot (112AM). The first housing middle slot (112AM) is connected to a first housing front opening (112AF. When the lock button (24A) is depressed by the user the middle pair of middle grooves engage the first housing middle slot (112AM) permitting the lock button (24A) to slide between the first housing rear opening (112AR) and the first housing front opening (112AF).

Figure 2:
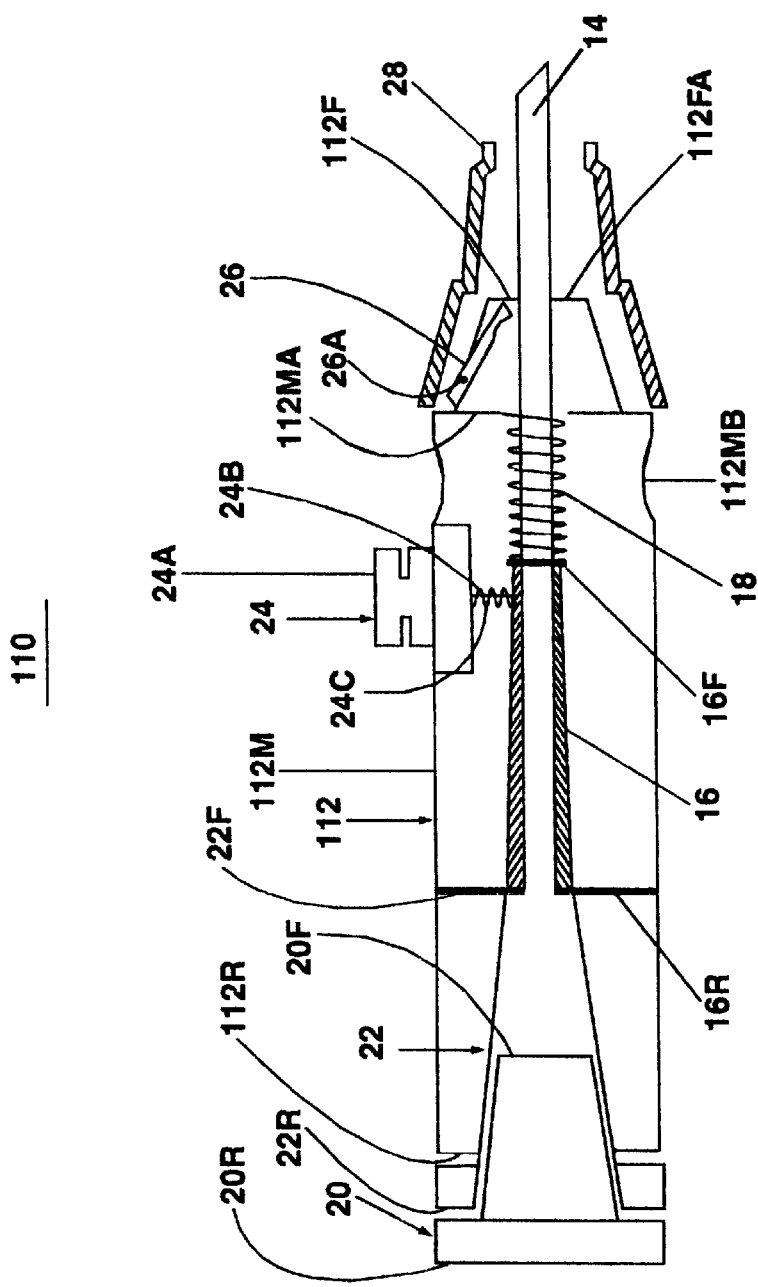
FIG. 2 is a cross-sectional view of a safety cannula with a needle in a safe position.
Figure 3:
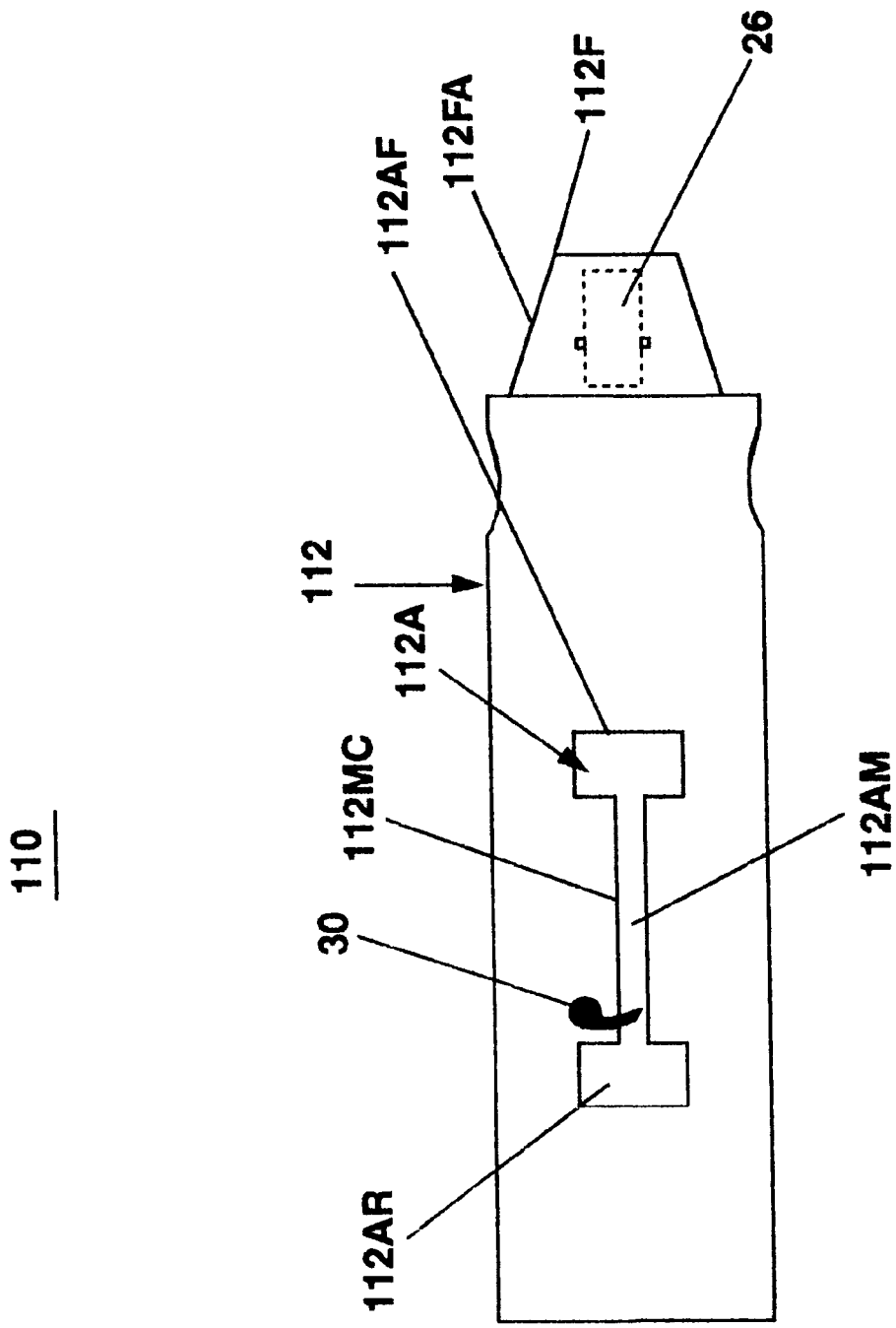
FIG. 3 is a top view of a safety cannula with a needle in a safe position.

Secondly, referring to FIG. 2 and FIG. 3 which is a cross-sectional view of a first safety cannula (110) with a needle (14) in a operable position. The first safety cannula (110) comprises a first housing (112) which comprises a first housing front (112F). The first housing front (112F) comprises a first housing front opening (112FA) centrally positioned therein. The first housing front (112F) further comprises a first housing rear (112R) having a first housing rear opening (112RA). The first housing front (112F) further comprises a first housing middle (112M) with a first housing middle divider (112MA) having an opening centrally positioned therein. The first housing middle (112M) further comprises a first housing middle indent (112MB) which functions as a gripping means. The first housing front (112F) further comprises a stopper (26) which is pivotally positioned on a stopper pin (26A). The first housing front (112F) further comprises a complimentary shaped removable catheter (28).

The first safety cannula (110) further comprises a needle (14) which is slidably positioned within the first housing (112). The needle (14) comprises a needle front (14F) and a needle rear (14R). The first safety cannula (110) further comprises a retainer (16) which is securely connected to the needle rear (14R). The retainer (16) comprises a retainer front (16F) and a retainer rear (16R). The first safety cannula (110) further comprises a first spring (18) which is positioned around the needle (14) between the retainer front (16F) and the first housing middle opening divider (112MA). The first safety cannula (110) further comprises a connector (22). The connector (22) comprises a connector rear (22R) and a connector front (22F) which are removably and securely positioned in the first housing rear opening (112RA). The connector rear (22R) and a connector front (22F) are sealably attached to the retainer rear (16R). The first safety cannula (110) further comprises a cap (20). The cap (20) comprises a cap front (20F) which is removably and securely positioned in the connector rear (22R). The cap (20) comprises cap rear (20R) which is connected to an IV tube. The first safety cannula (110) further comprises a lock (24) which is movably positioned in the first housing middle (112M). The lock (24) comprises a lock button (24A) having a lock pin (24B) securely attached thereto and extending therefrom. The lock (24) further comprises a lock spring (24C) which is positioned around the lock pin (24B) on an inside of the first housing middle (112M). The first safety cannula (110) further comprises a latch (30) which is pivotally attached to the first housing (112) within an operable distance of the lock (24). The latch (30) functions to releasably grip the lock button (24A) in a fill retracted position to prevent reextension of the needle (14). The needle (14) is extended by first releasing the latch (30) then moving the lock button (24A) to an extended position.

To place the first safety cannula (110) in a safe condition after use, a person depresses the lock button (24A) causing the middle pair of middle grooves to engage the first housing middle slot (112AM) permitting the first spring (18) to causing the needle (14) to move rearwardly and the lock button (24A) to slide between the first housing front opening (112AF) and the first housing rear opening (112AR).

The retainer (16) moves rearwardly because of the bias of the first spring (18) until the retainer rear (16R) makes contact with the first housing rear (112R) which moves the needle (14) rearwardly within the first housing (112) causing the needle front (14F) to be repositioned rearward of the first housing front opening (112FA) and the stopper (26). The stopper (26) moves inwardly blocking the first housing front opening (112FA) and thus, preventing the needle (14) from emerging therethrough. In this position inadvertent contact with the needle front (14F) is prevented.

Figure 4:
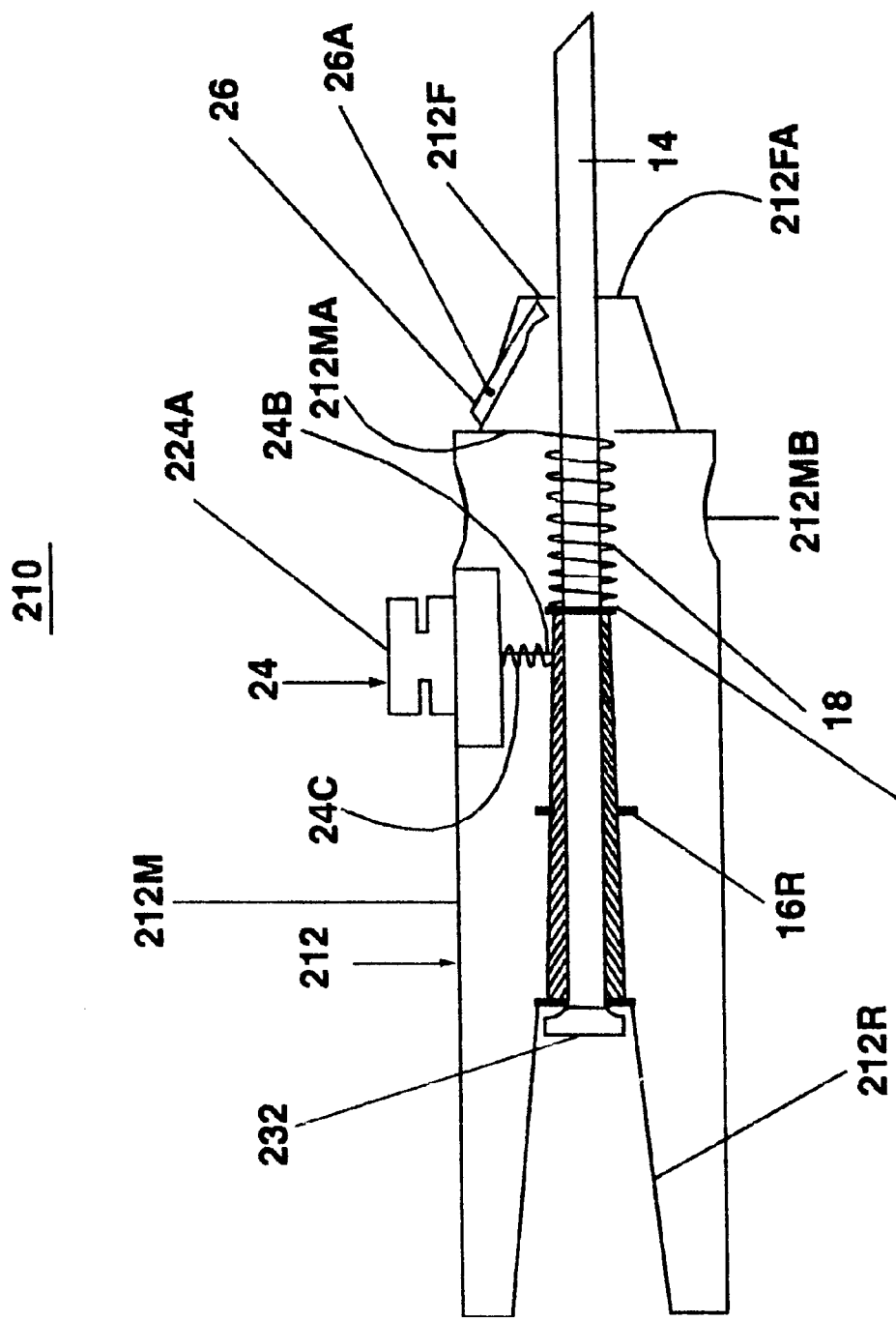
FIG. 4 is a cross-sectional view of a second safety cannula with a needle in a operable position.

Firstly, referring to FIG. 4 which is a cross-sectional view of a second safety cannula (210) with a needle (14) in a operable position. The second safety cannula (210) comprises a second housing (212) which comprises a second housing front (212F). The second housing front (212F) comprises a housing front opening (212FA) centrally positioned therein. The housing front (212F) further comprises a housing rear (212R) having a housing rear opening (212RA). The housing front (212F) further comprises a housing middle (212M) with a housing middle divider (212MA) having an opening centrally positioned therein. The housing middle (212M) further comprises a housing middle indent (212MB) which functions as a gripping means. The housing front (212F) further comprises a stopper (26) which is pivotally positioned on a stopper pin (26A).

The second safety cannula (210) further comprises a needle (14) which is slidably positioned within the housing (212). The needle (14) comprises a needle front (14F) and a needle rear (14R). The second safety cannula (210) further comprises a retainer (16) which is securely connected to the needle rear (14R). The retainer (16) comprises a retainer front (16F) and a retainer rear (16R). The second safety cannula (210) further comprises a first spring (18) which is positioned around the needle (14) between the retainer front (16F) and the housing middle opening divider (212MA).

The second safety cannula (210) further comprises a second cap (232). The second cap (232) is removably and securely positioned in the retainer rear (16R). The second cap (232) functions to permit testing the flow of fluids from the needle (14).

The second safety cannula (210) further comprises a lock (24) which is movably positioned in the housing middle (212M). The lock (24) comprises a lock button (24A) having a lock pin (24B) securely attached thereto and extending therefrom. The lock (24) further comprises a lock spring (24C) which is positioned around the lock pin (24B) on an inside of the housing middle (212M). The second safety cannula (210) further comprises a latch (30) which is pivotally attached to the housing (212) within an operable distance of the lock (24). The latch (30) functions to releasably grip the lock button (24A) in a full retracted position to prevent reextension of the needle (14). The needle (14) is extended by first releasing the latch (30) then moving the lock button (24A) to an extended position.

To place the second safety cannula (210) in a safe condition after use, a person depresses the lock button (24A) causing the middle pair of middle grooves to engage the housing middle slot (212AM) permitting the first spring (18) to causing the needle (14) to move rearwardly and the lock button (24A) to slide between the housing slot ront opening (212AF) and the housing slot rear opening (212AR).

The retainer (16) moves rearwardly because of the bias of the first spring (18) until the retainer rear (16R) makes contact with the housing rear (212R) which moves the needle (14) rearwardly within the housing (212) causing the needle front (14F) to be repositioned rearward of the housing front opening (212FA) and the stopper (26). The stopper (26) moves inwardly blocking the housing front opening (212FA) and thus, preventing the needle (14) from emerging therethrough. In this position inadvertant contact with the needle front (14F) is prevented.

Figure 5:
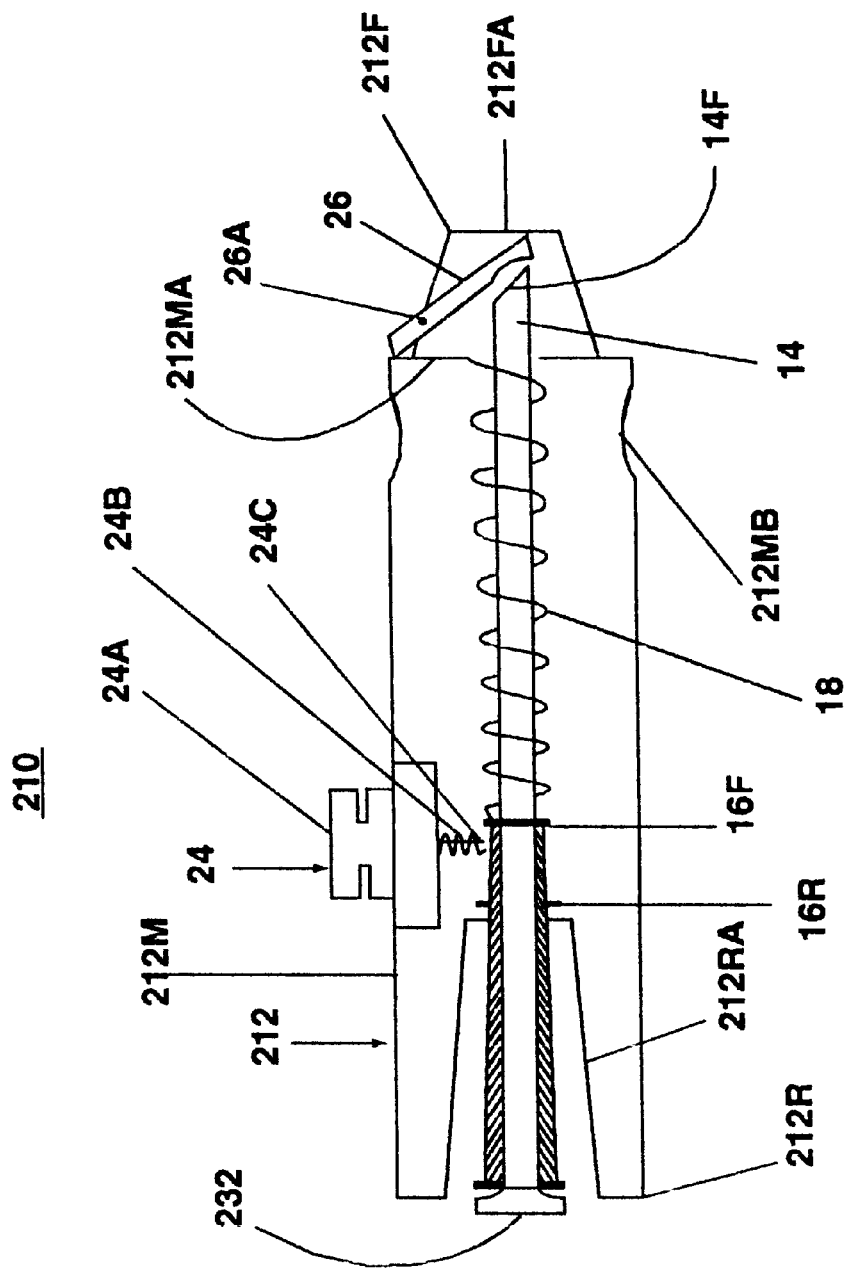
FIG. 5 is a cross-sectional view of a second safety cannula with a needle in a safe position.

Next, referring to FIG. 5 which is a cross-sectional view of a second safety cannula (210) with a needle (14) in a safe position. The second safety cannula (210) comprises a housing (212) which comprises a housing front (212F). The housing front (212F) comprises a housing front opening (212FA) centrally positioned therein. The housing front (212F) further comprises a housing rear (212R) having a housing rear opening (212RA). The housing front (212F) further comprises a housing middle (212M) with a housing middle divider (212MA) having an opening centrally positioned therein. The housing middle (212M) further comprises a housing middle indent (212MB) which functions as a gripping means.

The housing middle (212M) further comprises a housing slot rear opening (212AR) on an upper side which is connected to a housing middle slot (212AM). The housing middle slot (212AM) is connected to a housing front opening (212AF.

The housing front (212F) further comprises a stopper (26) which is pivotally positioned on a stopper pin (26A).

The second safety cannula (210) further comprises a needle (14) which is slidably positioned within the housing (212). The needle (14) comprises a needle front (14F) and a needle rear (14R). The second safety cannula (210) further comprises a retainer (16) which is securely connected to the needle rear (14R). The retainer (16) comprises a retainer front (16F) and a retainer rear (16R). The second safety cannula (210) further comprises a first spring (18) which is positioned around the needle (14) between the retainer front (16F) and the housing middle opening divider (212MA).

The second safety cannula (210) further comprises a second cap (232). The second cap (232) is removably and securely positioned in the retainer rear (16R). The second cap (232) functions to permit testing the flow of fluids from the needle (14).

The second safety cannula (210) further comprises a lock (24) which is movably positioned in the housing middle (212M). The lock (24) comprises a lock button (24A) having a middle pair of middle grooves and having a lock pin (24B) securely attached thereto and extending therefrom. The lock (24) further comprises a lock spring (24C) which is positioned around the lock pin (24B) on an inside of the housing middle (212M). The lock button (24A) is slidable attached to the housing slot rear opening (212AR) which is connected to a housing middle slot (212AM). The housing middle slot (212AM) is connected to a housing front opening (212AF). When the lock button (24A) is depressed by the user the middle pair of middle grooves engage the housing middle slot (212AM) permitting the lock button (24A) to slide between the housing slot rear opening (212AR) and the housing slot ront opening (212AF).

It will be understood that each of the elements described above, or two or more together, may also find a useful application in other types of constructions differing from the type described above.

While the invention has been illustrated and described as embodied in a safety cannula, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A first safety cannula (110) comprising:
A) a first housing (112) which comprises a first housing front (112F) having a first housing front opening (112FA) centrall positioned therein, a first housing rear (112R) having a first housing rear opening (112RA) and a first housing middle (112M) with a first housing middle divider (112MA) having an opening centrally positioned therein;
B) a needle (14) slidably positioned within the first housing (112), the needle (14) comprises a needle front (14F) and a needle rear (14R);
C) a retainer (16) securely connected to the needle rear (14R), the retainer (16) comprises a retainer front (16F) and a retainer rear (16R);
D) a first spring (18) is positioned around the needle (14) between the retainer front (16F) and the first housing middle opening divider (112MA);
E) a connector (22) comprises a connector rear (22R) and a connector front (22F) removably securely positioned in the first housing rear opening (112RA) and sealably attached to the retainer rear (16R);
F) a cap (20) comprises a cap front (20F)removably securely positioned in the connector rear (22R) and a cap rear (20R) connected to an IV tube; and
G) a lock (24) is movably positioned in the first housing middle (112M), the lock (24) comprises a lock button (24A) having a lock pin (24B) securely attached thereto extending therefrom, the lock (24) further comprises a lock spring (24C) positioned around the lock pin (24B) on an inside of the first housing middle (112M), after the first safety cannula (110) is used, a person lifts upwardly on the lock button (24A) which lifts the lock pin (24B) which is positioned rearwardly against the retainer front (16F), the retainer (16) moves rearwardly until the retainer rear (16R) hits the first housing rear (112R), concurrently, the needle (14) retracts within the first housing (112).

2. The first safety cannula (110) as described in claim 1, wherein the first housing middle (112M) further comprises a first housing middle indent (112MB) which functions as a gripping means.

3. The first safety cannula (110) as described in claim 1, wherein the first housing front (112F) further comprises a stopper (26) pivotally positioned on a stopper pin (26A), when the needle retracts into the first housing (112), the stopper (26) moves inwardly blocking the first housing front opening (112FA) and thus, preventing the needle (14) from emerging therethrough.

4. The first safety cannula (110) as described in claim 1, wherein the first housing front (112F) further comprises a complimentary shaped removable catheter (28).

5. A second safety cannula (210) comprising:
A) a second housing (212) which comprises a second housing front (212F) having a second housing front opening (212FA) centrall positioned therein, a second housing rear (212R) having a second housing rear opening (212RA) and a second housing middle (212M) with a second housing middle divider (212MA) having an opening centrally positioned therein;
B) a needle (14) slidably positioned within the second housing (212), the needle (14) comprises a needle front (14F) and a needle rear (14R);
C) a retainer (16) securely connected to the needle rear (14R), the retainer (16) comprises a retainer front (16F) and a retainer rear (16R);
D) a first spring (18) is positioned around the needle (14) between the retainer front (16F) and the second housing middle opening divider (212MA);
E) a cap (20) which removably securely positioned in the second housing rear opening (212RA) and sealably attached to the retainer rear (16R);
F) a lock (24) is movably positioned in the second housing middle (212M), the lock (24) comprises a lock button (24A) having a lock pin (24B) securely attached thereto extending therefrom, the lock (24) further comprises a lock spring (24C) positioned around the lock pin (24B) on an inside of the second housing middle (212M), after the second safety cannula (210) is used, a person lifts upwardly on the lock button (24A) which lifts the lock pin (24B) which is positioned rearwardly against the retainer front (16F), the retainer (16) moves rearwardly until the retainer rear (16R) hits the second housing rear (212R), concurrently, the needle (14) retracts within the second housing (212).

6. The second safety cannula (210) as described in claim 5, wherein the second housing middle (212M) further comprises a second housing middle indent (212MB) which functions as a gripping means.

7. The second safety cannula (210) as described in claim 5, wherein the second housing front (212F) further comprises a stopper (26) pivotally positioned on a stopper pin (26A), when the needle retracts into the second housing (212), the stopper (26)moves inwardly blocking the second housing front opening (212FA) and thus, preventing the needle (14) from emerging therethrough.

8. The second safety cannula (210) as described in claim 5, wherein the second housing front (212F) further comprises a complimentary shaped removable catheter (28).

9. The second safety cannula (210) as described in claim 5, wherein the second housing middle (212M) further comprises a second housing rear opening (212AR) which is connected to a second housing middle slot (212AM) which is connected to a housing slot front opening (212AF), and wherein the lock button (24A) comprises a pair of grooves which when the lock button (24A) is depressed slidably engades a second housing middle slot (212AM) permitting the lock button (24A) move between the housing slot front opening (212AF) and the second housing rear opening (212AR) housing slot front opening (212AF).

* * * * *